(12) United States Patent
Singhal

(10) Patent No.: US 10,828,416 B2
(45) Date of Patent: Nov. 10, 2020

(54) APPARATUS AND METHODS FOR REUSE OF INJECTION NEEDLE FOR HOME USERS

(76) Inventor: Tara Chand Singhal, Torrance, CA (US)

(*) Notice: Subject to any disclaimer, the term of this patent is extended or adjusted under 35 U.S.C. 154(b) by 1103 days.

(21) Appl. No.: 12/807,481

(22) Filed: Sep. 7, 2010

(65) Prior Publication Data

US 2012/0059333 A1 Mar. 8, 2012

(51) Int. Cl.
*A61M 5/00* (2006.01)
*A61M 5/32* (2006.01)
*A61M 5/24* (2006.01)
*A61M 5/34* (2006.01)

(52) U.S. Cl.
CPC .......... *A61M 5/001* (2013.01); *A61M 5/2466* (2013.01); *A61M 5/3202* (2013.01); *A61M 5/3213* (2013.01); *A61M 5/3293* (2013.01); *A61M 5/347* (2013.01); *A61M 2005/2474* (2013.01); *A61M 2005/3206* (2013.01); *A61M 2005/3208* (2013.01); *A61M 2205/0205* (2013.01); *A61M 2205/0222* (2013.01)

(58) Field of Classification Search
CPC .. A61M 5/001; A61M 5/3202; A61M 5/3213; A61M 5/3293; A61M 5/347; A61M 2205/0222; A61M 2205/0205; A61M 5/50; A61M 5/3204; A61L 2202/23; A61L 2/00
USPC ....... 604/171, 172, 188, 192, 199, 403, 506; 206/362, 365
See application file for complete search history.

(56) References Cited

U.S. PATENT DOCUMENTS

| | | | | |
|---|---|---|---|---|
| 2,400,722 A | * | 5/1946 | Swan | A61M 5/001 206/210 |
| 2,616,420 A | * | 11/1952 | Hart | C01C 1/248 604/193 |
| 2,735,427 A | * | 2/1956 | Sullivan | 604/135 |

(Continued)

FOREIGN PATENT DOCUMENTS

| EP | 0 045 616 A1 | 7/1981 |
|---|---|---|
| EP | 0 615 768 A2 | 1/1994 |

(Continued)

OTHER PUBLICATIONS

PCT International Search Report and the written opinion of the International Searching Authority, or declaration dated Feb. 15, 2012 for PCT/US2011/050547.

*Primary Examiner* — Bhisma Mehta
*Assistant Examiner* — Hong-Van N Trinh
(74) *Attorney, Agent, or Firm* — Steve Roeder Esq

(57) ABSTRACT

A device for an injection needle that enables reuse of a single-use injection needle for multiple injection uses for a same user is described. The device has a needle cover with a disinfecting agent, a sanitizing agent and a lubricating agent that are positioned inside the needle cover. The needle cover sanitizes, disinfects and lubricates a single-use injection needle for reuse when the needle is moved inside the needle cover and positioned therein for temporary storage. The agents are held in a medium that enable the agents to be positioned inside the needle cover. The agents in the medium are stacked on top of each other in heights for different needle lengths. The first stack is a wick medium that absorbs excess fluid droplets from a needle head, the second stack is a medium that disinfects the needle, and the third stack is a medium that lubricates the needle.

18 Claims, 17 Drawing Sheets

(56) References Cited

U.S. PATENT DOCUMENTS

| | | | | | |
|---|---|---|---|---|---|
| 2,828,742 | A | * | 4/1958 | Ashkenaz | A61M 5/288 |
| | | | | | 604/193 |
| 3,413,974 | A | * | 12/1968 | Cohen | A61M 5/34 |
| | | | | | 604/201 |
| 4,178,930 | A | * | 12/1979 | Fisher, Jr. | A61M 5/34 |
| | | | | | 604/192 |
| 4,303,069 | A | * | 12/1981 | Cohen | A61M 5/288 |
| | | | | | 604/192 |
| 4,416,663 | A | * | 11/1983 | Hall | 604/198 |
| 4,695,274 | A | * | 9/1987 | Fox | 604/198 |
| 4,758,230 | A | * | 7/1988 | Rycroft | A61M 5/282 |
| | | | | | 206/366 |
| 4,915,697 | A | * | 4/1990 | DuPont | A61M 5/326 |
| | | | | | 604/192 |
| 5,190,521 | A | * | 3/1993 | Hubbard | A61M 5/422 |
| | | | | | 604/117 |
| 5,342,320 | A | * | 8/1994 | Cameron | 604/192 |
| 5,403,288 | A | * | 4/1995 | Stanners | 604/232 |
| 5,505,694 | A | * | 4/1996 | Hubbard | A61M 5/282 |
| | | | | | 604/242 |
| 5,876,380 | A | * | 3/1999 | Manganini et al. | 604/191 |
| 5,964,731 | A | * | 10/1999 | Kovelman | 604/110 |
| 6,203,529 | B1 | * | 3/2001 | Gabriel et al. | 604/192 |
| 2009/0187204 | A1 | * | 7/2009 | Schraga | 606/182 |
| 2012/0029469 | A1 | * | 2/2012 | Horvath et al. | 604/506 |

FOREIGN PATENT DOCUMENTS

| | | |
|---|---|---|
| FR | 2 571 972 A1 | 10/1984 |
| FR | 2571972 | 10/1984 |
| GB | 2 232 601 A | 6/1989 |
| WO | WO 2010/090747 A1 | 8/2010 |

* cited by examiner

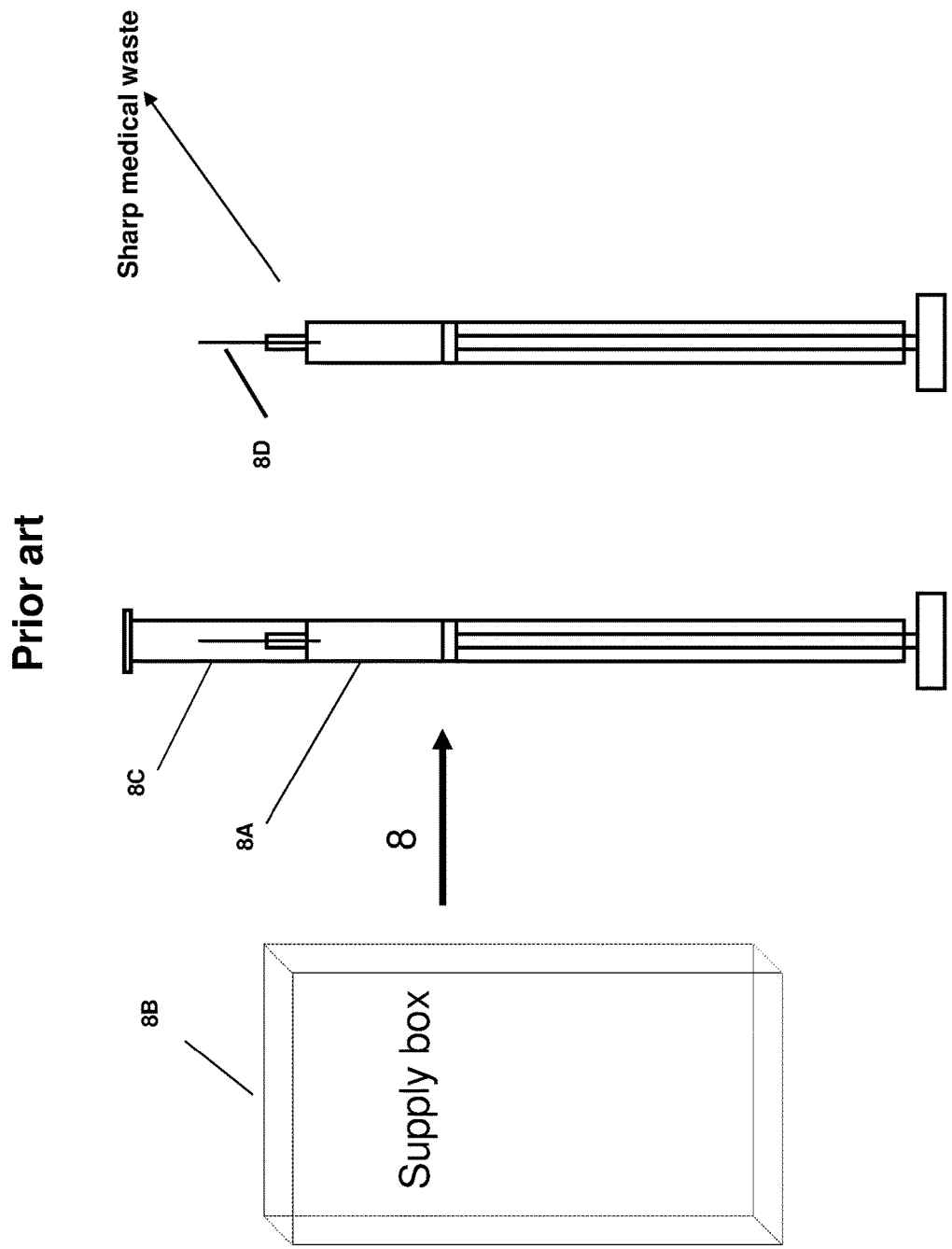

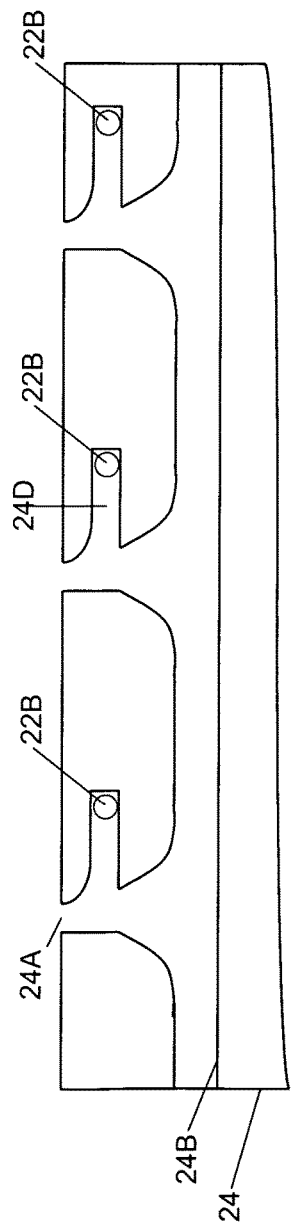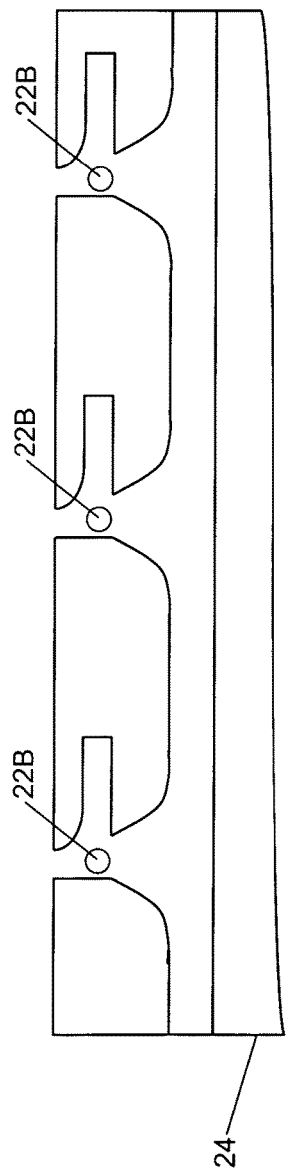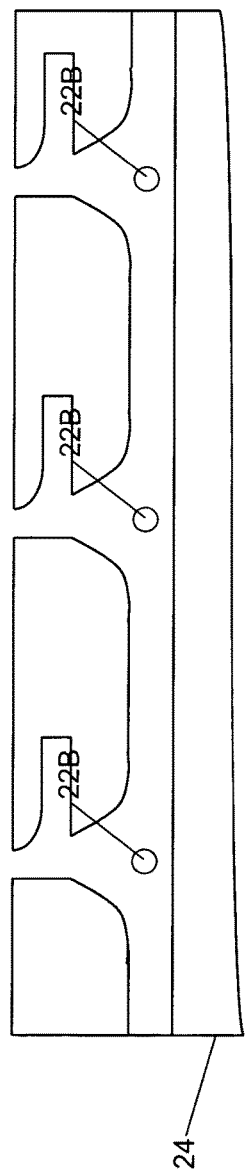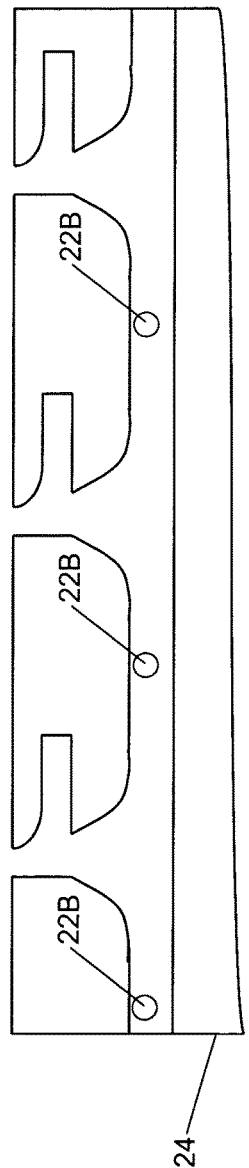

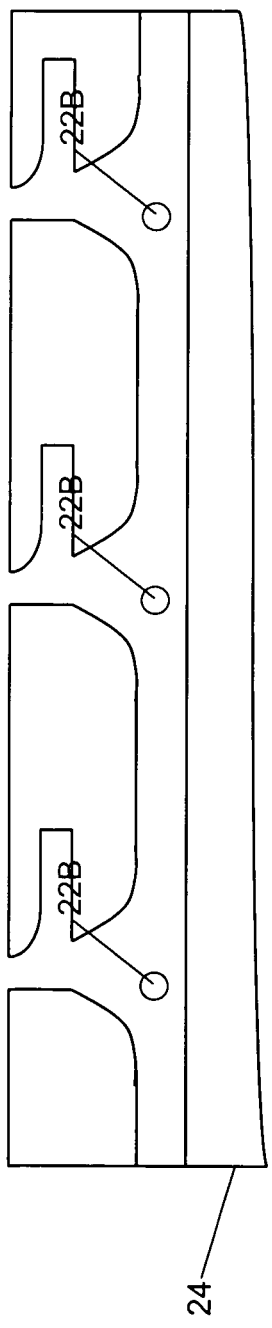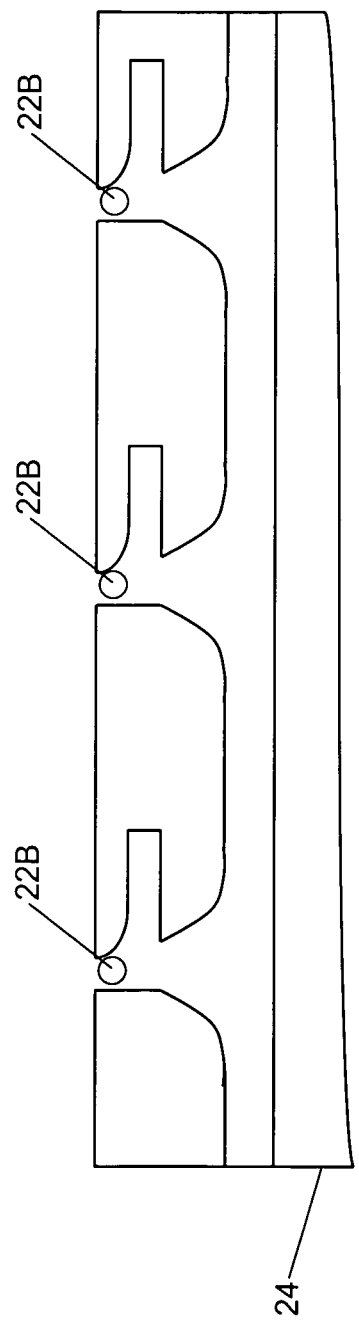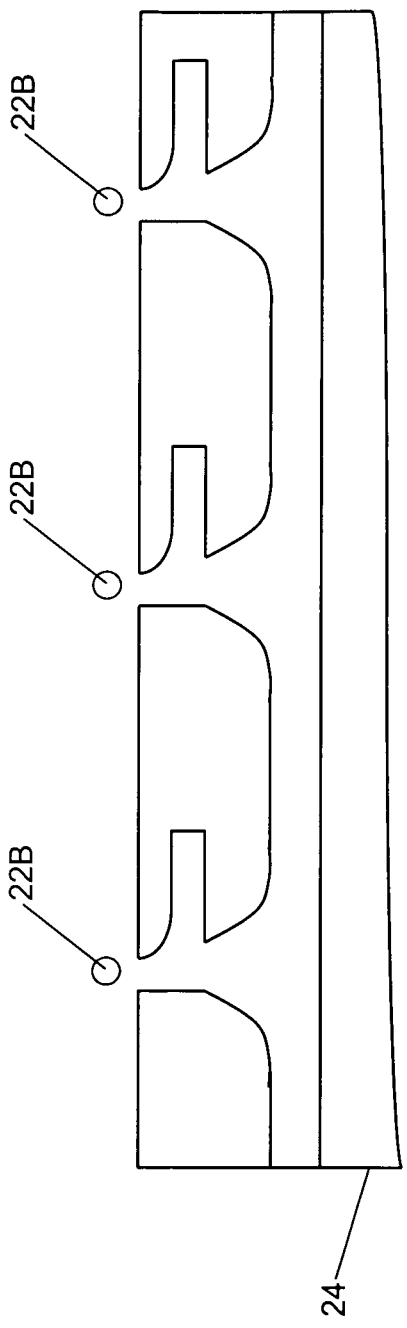

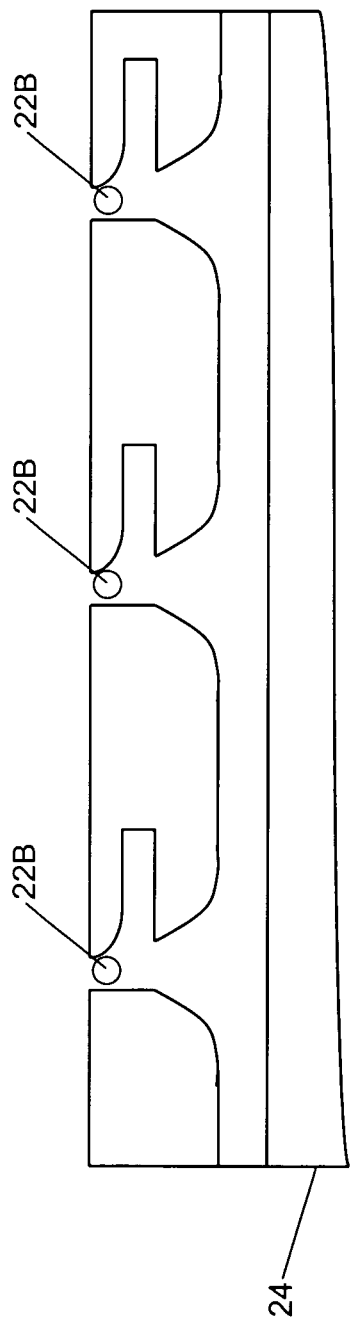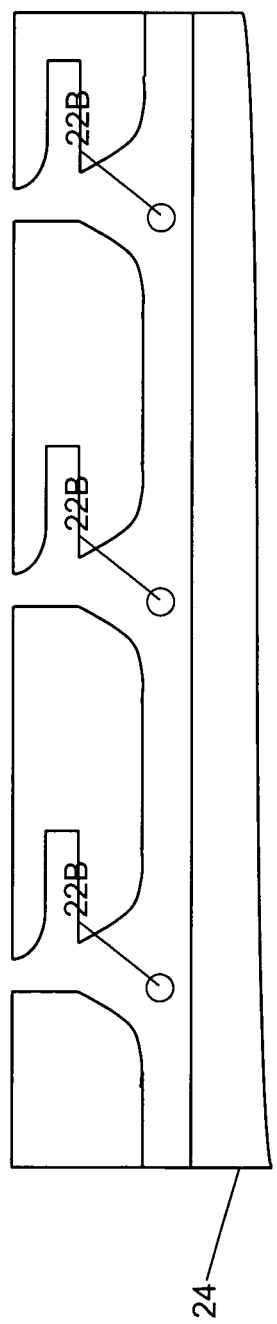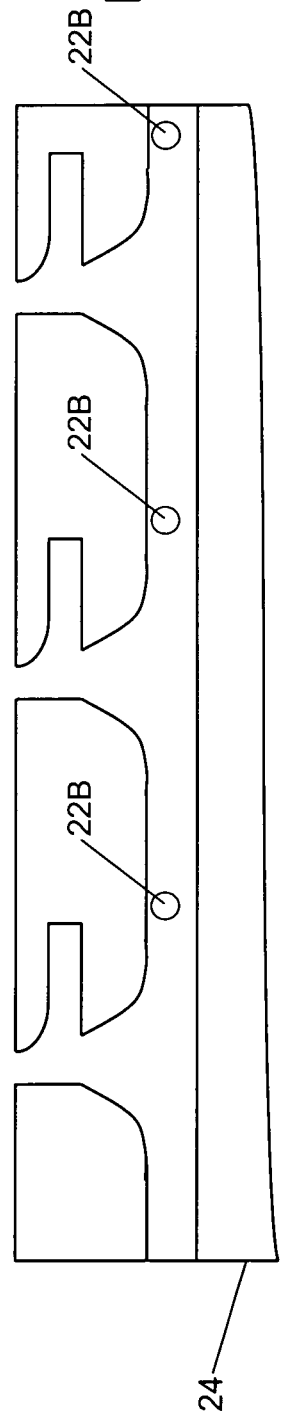

| |
|---|
| having a needle cover for an injection needle. 106 |
| positioning a needle storage medium inside the needle cover. 108 |
| inserting the injection needle inside the needle cover and the NSM for temporary storage 110 |
| removing the injection needle for next use. 112 |
| having in the plug a wicking medium, a disinfecting medium, and a lubricating medium. 114 |
| having a guide mechanism for guiding the needle inside the needle cover. 116 |
| having a sliding guide mechanism for guiding the injection needle inside the needle cover for injection needles mounted on syringes. 118 |
| having a (i) sliding guide mechanism for guiding the removal and installation of the needle cover with the injection needle inside, to a vial head of a pen dispenser and (ii) a rotary mechanism for screwing and unscrewing the needle inside the needle cover on to and from the vial head, for injection needles made for a pen dispenser use. 120 |
| having a storage mechanism for the needle cover with the needle inside in a housing of the pen dispenser. 122 |

Figure 6B

| molding an injection needle cover with a guide mechanism in the needle cover for guiding the needle cover on to a needle. 124 |
|---|
| inserting a needle storage medium inside the needle cover. 126 |
| molding a male part of the guide mechanism in the needle cover and a female part in the syringe for a syringe injector. 128 |
| molding a male part of the guide mechanism in the needle cover and a female part in the pen injector housing. 130 |

Figure 6C

APPARATUS AND METHODS FOR REUSE OF INJECTION NEEDLE FOR HOME USERS

CROSS REFERENCE

None

FIELD OF THE INVENTION

Described are apparatus and methods for preparing for reuse, single-use disposable syringes and needles for a home user, to reduce the cost of such disposables and to reduce the effort and the infrastructure cost of disposing sharp medical waste.

BACKGROUND

Based on one statistic, there are approx. 9 million syringe users. Nearly two-thirds of these at-home injectors are for people with diabetes and patients administering home health treatments for a variety of diseases. The problems associated with such syringe uses are two fold. One is the cost of one-time use disposable syringes, which is borne by the health care system and ultimately the patient. The second is the effort and the cost of the infrastructure for the safe disposable of the sharp medical waste. The majority of these "community needles" are discarded into the public solid waste system, posing a risk of injury and infection to anyone who encounters them.

Governments have come to realize the problem associated with safe disposable of sharp medical waste as the people on their own discard such waste in the household waste. Despite the growing problems associated with improper disposal of sharps outside health care facilities, there are no consistent regulations or guidelines for their safe disposal.

Current EPA guidelines, suggest disposing all sharps (needles, lancets, syringes) in a household plastic container or coffee can, secure the lid and write do not recycle on the outside and simply deposit in household trash. Unfortunately, this does not take the needle out of the waste stream—it simply ends up in the general household trash putting neighbors, children and waste workers at risk of needle stick injuries.

Laws at State level have been enacted to address this problem. As an illustration of the magnitude of this problem of sharp medical waste disposal, following excerpts from a California law SB 1305 are quoted below.

SB 1305, Figueroa The Medical Waste Management Act.

This bill would, on or after Sep. 1, 2008, prohibit a person from knowingly placing home-generated sharps waste in certain types of containers, provide that home-generated sharps waste shall be transported only in a sharps container, as defined in the act, or other container approved by the department or local enforcement agency, and provide that this waste shall only be managed at specified locations consistent with existing law.

THE PEOPLE OF THE STATE OF CALIFORNIA DO ENACT AS FOLLOWS:

SECTION 1. The Legislature finds and declares all of the following:

(a) The development of a safe, convenient, and cost-effective infrastructure for the collection of millions of home-generated sharps, and the public education programs to promote safe disposal of these sharps, will require a cooperative effort by the State Department of Health Services, the California Integrated Waste Management Board, local governments, large employers, dispensing pharmacies, as well as health care, solid waste, pharmaceutical industries, and manufacturers of sharps.

SEC. 2. Section 117671 is added to the Health and Safety Code, to read:

117671. "Home-generated sharps waste" means hypodermic needles, pen needles, intravenous needles, lancets, and other devices that are used to penetrate the skin for the delivery of medications derived from a household, including a multifamily residence or household.

SEC. 4. Section 118286 is added to the Health and Safety Code, to read:

118286. (a) On or after Sep. 1, 2008, no person shall knowingly place home-generated sharps waste in any of the following containers:

(1) Any container used for the collection of solid waste, recyclable materials, or green-waste.

(2) Any container used for the commercial collection of solid waste or recyclable materials from business establishments.

(3) Any roll-off container used for the collection of solid waste, construction, and demolition debris, green-waste, or other recyclable materials.

(b) On or after Sep. 1, 2008, home-generated sharps waste shall be transported only in a sharps container, or other containers approved by the enforcement agency, and shall only be managed at any of the following:

(1) A household hazardous waste facility pursuant to Section 25218.13.

(2) A "home-generated sharps consolidation point" as defined in subdivision (b) of Section 117904.

(3) A medical waste generator's facility pursuant to Section 118147.

(4) A facility through the use of a medical waste mail-back container approved by the department pursuant to subdivision (b) of Section 118245.

It is the objective of the preferred embodiments to address the problems associated with the use of at home syringes and needles for the users. It is the objective to reduce the cost to the users directly and health care system indirectly of the disposable syringes and needles for home use. It is yet another objective to reduce the effort and cost of the infrastructure for disposing such sharp medical waste as required by the State laws. It is yet another objective to make task of using injections less cumbersome and with fewer steps.

SUMMARY

With reference to FIGS. 1A, 1B, and 1C, the problems associated with the use of at-home injections is summarized here. These figures are labeled as prior art. There are two types of injectors for home use. One injector is used with a pen-like insulin delivery device, as illustrated in FIGS. 1A and 1B, where the needle is screwed on to a vial head of the pen like delivery device. The other injector is a syringe as in FIG. 1C, where the needle is permanently attached to the syringe.

With reference to FIG. 1A, to use a pen like device, a pen like device 2 is used. The device 2 has an insulin vial 2C with a vial head 2D, a pen body 2A, and cap/cover 2B for the vial for storage when the device 2 is not in use. Also shown is a box of needles 6 that has needles 4 for use with the pen device 2. The device 2 and needle 4 are manufactured and sold by different companies. One manufacturer of the pen-like device is Lilly and one manufacturer of the needles is Becton-Dickinson (BD). The needle 4 has a needle cover 4A, a needle cap 4B, a needle 4C and a sealer 4D at the bottom of the needle cover 4A.

The use of such a pen device 2 with a needle 4 requires the following steps as shown with encircled numerals in FIGS. 1A and 1B. At step 1, a pen device 2 is used where the cover 2B is removed exposing the vial head 2D as in step 2. In step 3A a box of needle supply is at hand to get a needle 4 for use. At step 3B, the sealer 4D of the needle cover 4A is peeled of and the needle cover 4A is placed on the top of the vial head, pushed down and then screwed clockwise to attach the needle 4C to the vial head 2B. At step 4, the needle cover 4A of the needle is pulled away, exposing the needle 4C with the needle cap 4B on. At step 5, the needle cap 4B is pulled away exposing the needle 4C for use.

After the needle 4C is used for injection, at step 6A, the needle cover 4A is aligned on top of the exposed needle 4C and pushed down on top of the needle and screwed counter-clockwise to engage the needle 4C inside the needle cover 4A and the needle cover 4A is pulled away from the pen to remove the needle 4C from the vial head 2B. At step 6B, the needle 4C inside needle cover 4A is discarded as a sharp medical waste in a special waste container. At step 7, the cover 2B of the pen-device 2 is placed back on pen 2 for storage of the pen 2 until next use.

With reference to FIG. 10, a syringe 8 is shown that is gotten from a supply box 8B. The syringe 8 has a syringe body 8A with an attached needle 8D and a removable needle cover 8C. For the use of the syringe 8, the needle cover 8C is first removed by pulling it away from the syringe body to expose the needle 8D. The syringe body 8A with the exposed needle 8C is then used to draw medicine from a bottle for injection into the body. After use, the syringe 8 is discarded as a sharp medical waste in a sharp medical waste container.

As has been described and summarized above in the background section, there are primarily two issues associated with the use of the single use disposable injectors. One is the cost of the disposable injectors, which retail at about 30 cents a piece. An average home user may be injecting on average 100 times a month, making the cost of the supply at around $30 a month. The second issue is the effort and the cost of infrastructure for disposal of such sharp medical waste.

The disposable injection manufacturing industry has been focused on reducing the pain of such injections. They have done that three different ways. One way has been by reducing the thickness of the needle, other way has been by making the needle tip beveled and the third way has been by coating the needle with a lubricant. Each needle is made of a special steel alloy and is identified as 31G/5B, where the number 31 represents the thickness based on AWG standard and 5 represents the number of bevels on the tip of the needle. The AWG 31 equates to a thickness of 0.2261 millimeters. Earlier generation of such needles, were identified as 27G/3B, where 27 was the AWG thickness and 3 was the number of bevels.

The industry that manufactures these syringes with attached needles and needles for pen injectors states two reasons for not to reuse such single use needles. One stated reason is the risk of infection from reuse and the second stated reason is the probable extra pain of the injection, as each needle is lubricated for reducing pain of injection and that the lubricating coating on the needle is worn out with a single use.

The preferred embodiments teach a device that enables the reuse of such syringes with attached needles and the pen injector needles for a limited number of reuses for a home user that alleviate these two potential concerns.

In a preferred embodiment, for the needles, used in pen type injectors, the needle cover is provided a needle storage medium (NSM) inside the needle cover that prepares the needle for reuse while it is stored there between uses. In another similar embodiment, for syringes with attached needles, the needle cover also has a needle storage medium (NSM) inside the needle cover that prepares the needle for reuse while the needle is stored there for reuse. The needle storage medium (NSM) in these embodiments provides a medium for sanitizing, disinfecting, and lubricating the needle between uses.

In another embodiment, in the use of pen type needle injectors, the needle is stored as part of the pen injector itself in between uses and thus its use is made easier for not having to store or carry the needle as a separate item with the pen injector. In the prior art the pen injector has no provision to store such needles.

The preferred embodiments are for an apparatus for injection needle that has a device that enables reuse of a single-use injection needle for multiple injection uses for a same user. The device has a needle cover with a disinfecting agent, a sanitizing agent and a lubricating agent that are positioned inside the needle cover. The needle cover sanitizes, disinfects and lubricates a single-use injection needle for reuse when the needle is moved inside the needle cover and positioned therein for temporary storage. The agents are held in a medium that enable the agents to be positioned inside the needle cover. The agents in the medium are stacked on top of each other in heights for different needle lengths. The first stack is a wick medium that absorbs excess fluid droplets from a needle head, the second stack is a medium that disinfects the needle, and the third stack is a medium that lubricates the needle.

These and other aspects of the preferred embodiments are described in detail with the help of the accompanying drawings and the description.

BRIEF DESCRIPTION OF THE DRAWINGS

Some of the novel features of the embodiments will be best understood from the accompanying drawings, taken in conjunction with the accompanying description, in which similar reference characters refer to similar parts, and in which:

FIG. 1A-C are block diagrams that illustrates features of the prior art for the injection of drugs using single use needles and syringes.

FIG. 5A-5M, are opened out block diagrams that illustrates features of a preferred embodiment for use of a needle cover with a pen delivery system with different positions of the needle cover in the vial housing.

FIG. 6A-C are method diagrams for a needle cover of the preferred embodiment.

DESCRIPTION

Figure 1A:
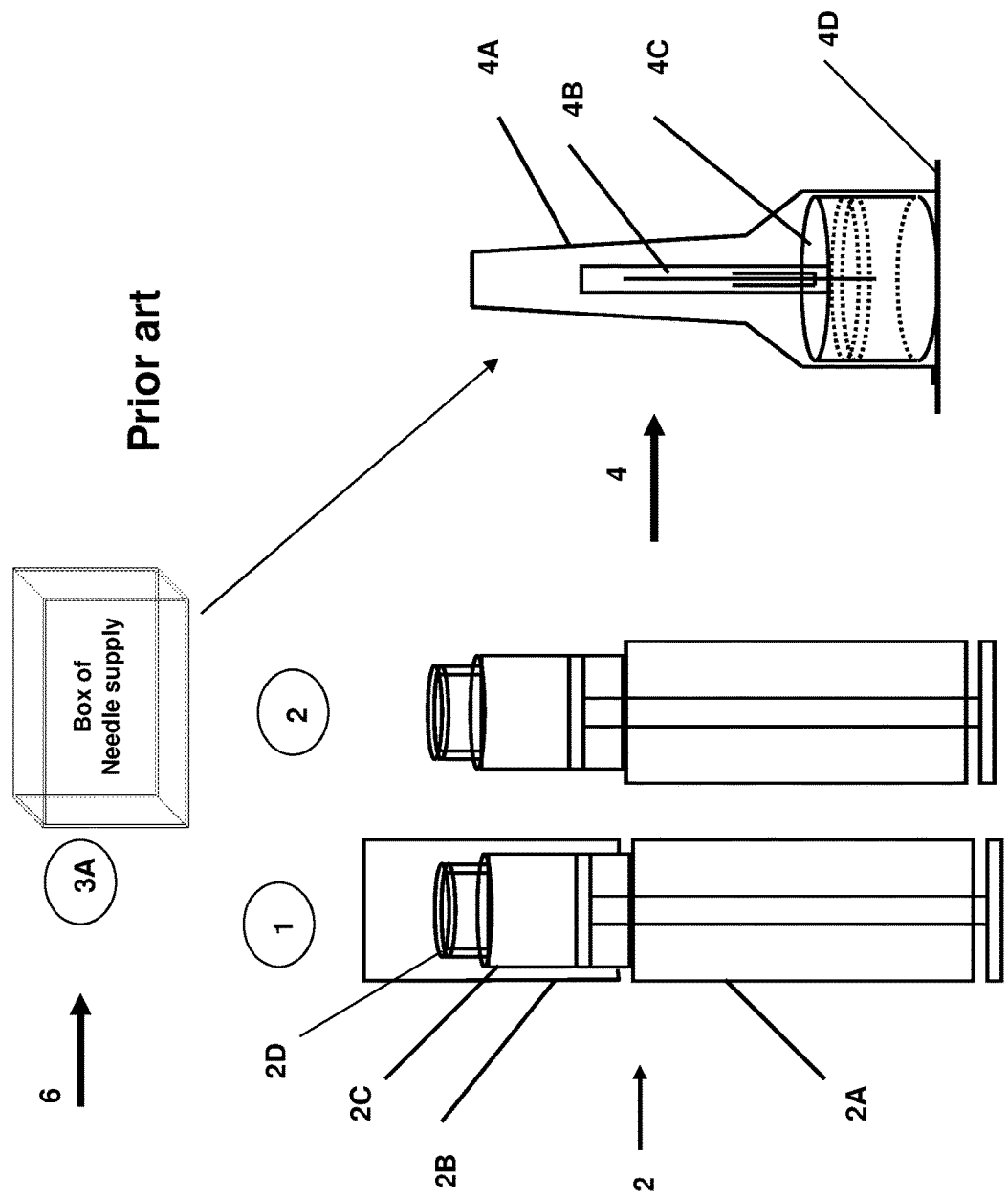
Figure 1B:
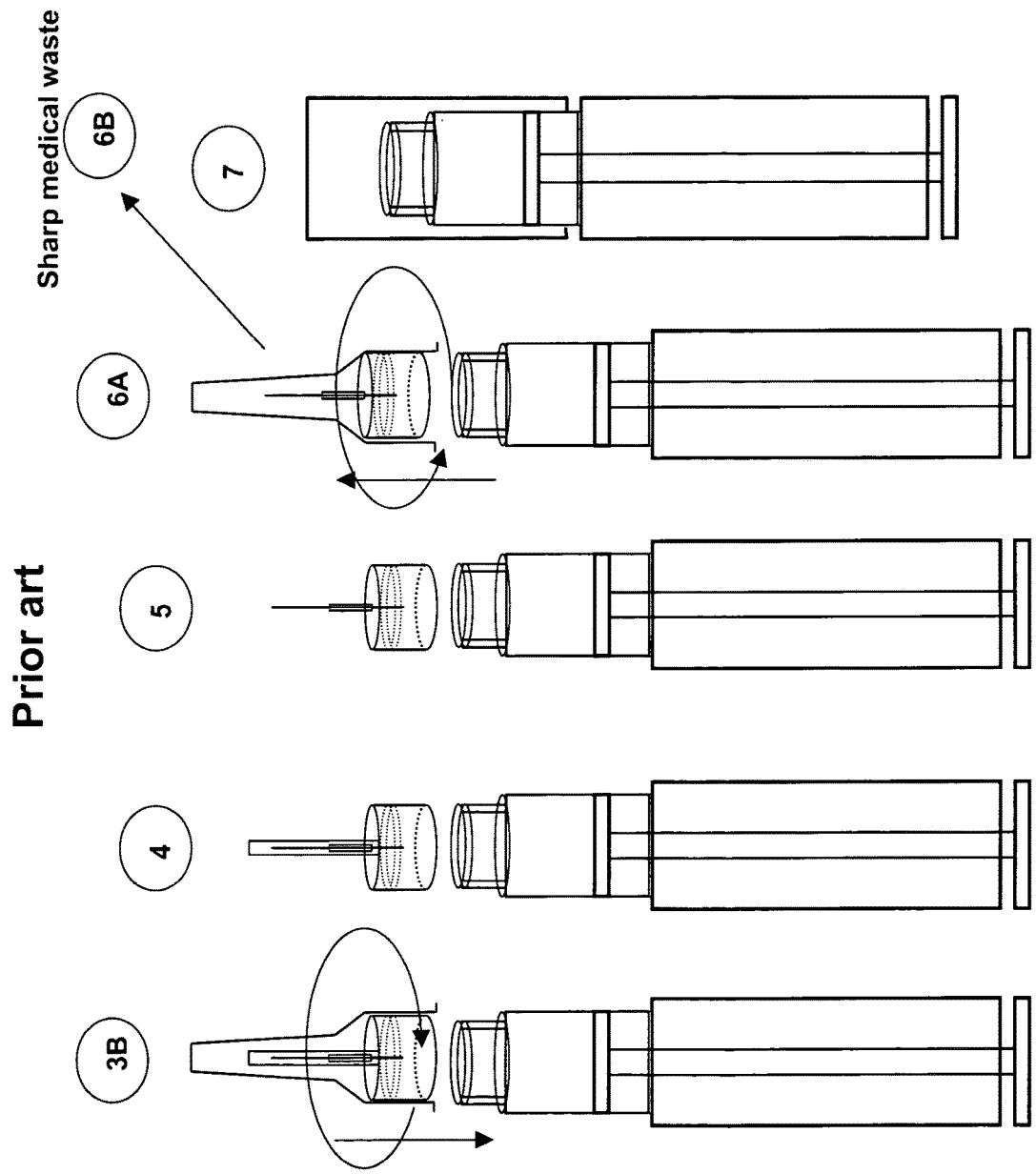
Figure 2A:
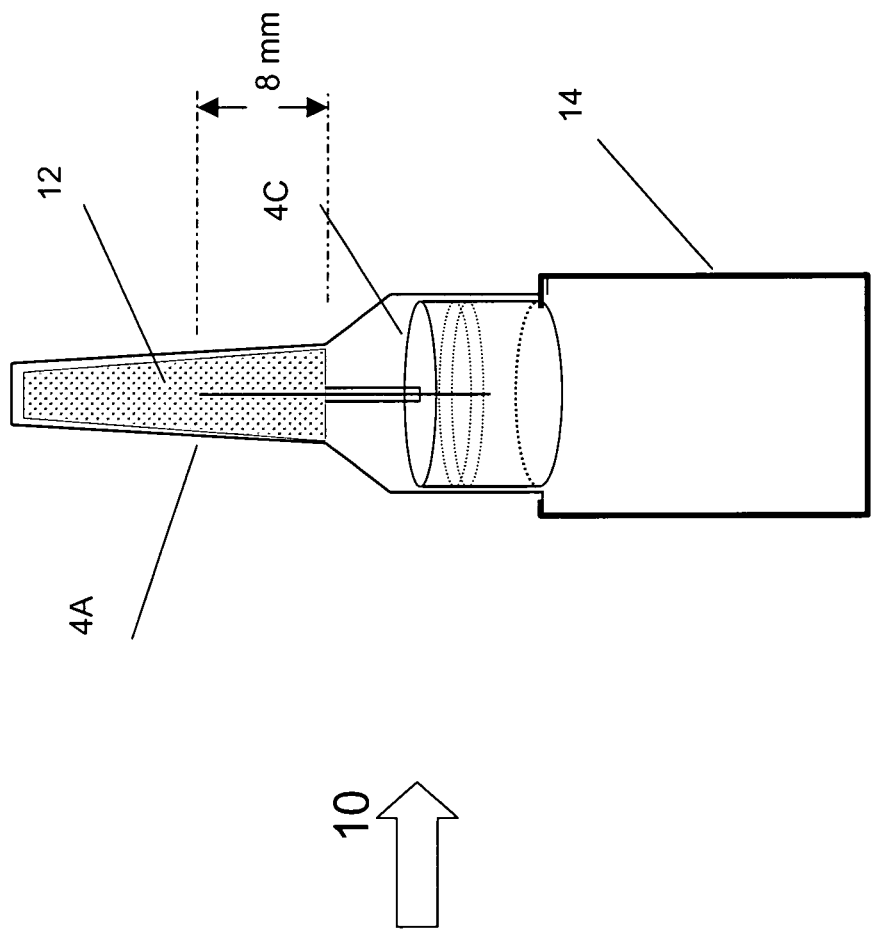
FIG. 2A-D are block diagrams that illustrates features of a preferred embodiment of a needle cover for reuse of single use injections.
Figure 2B:
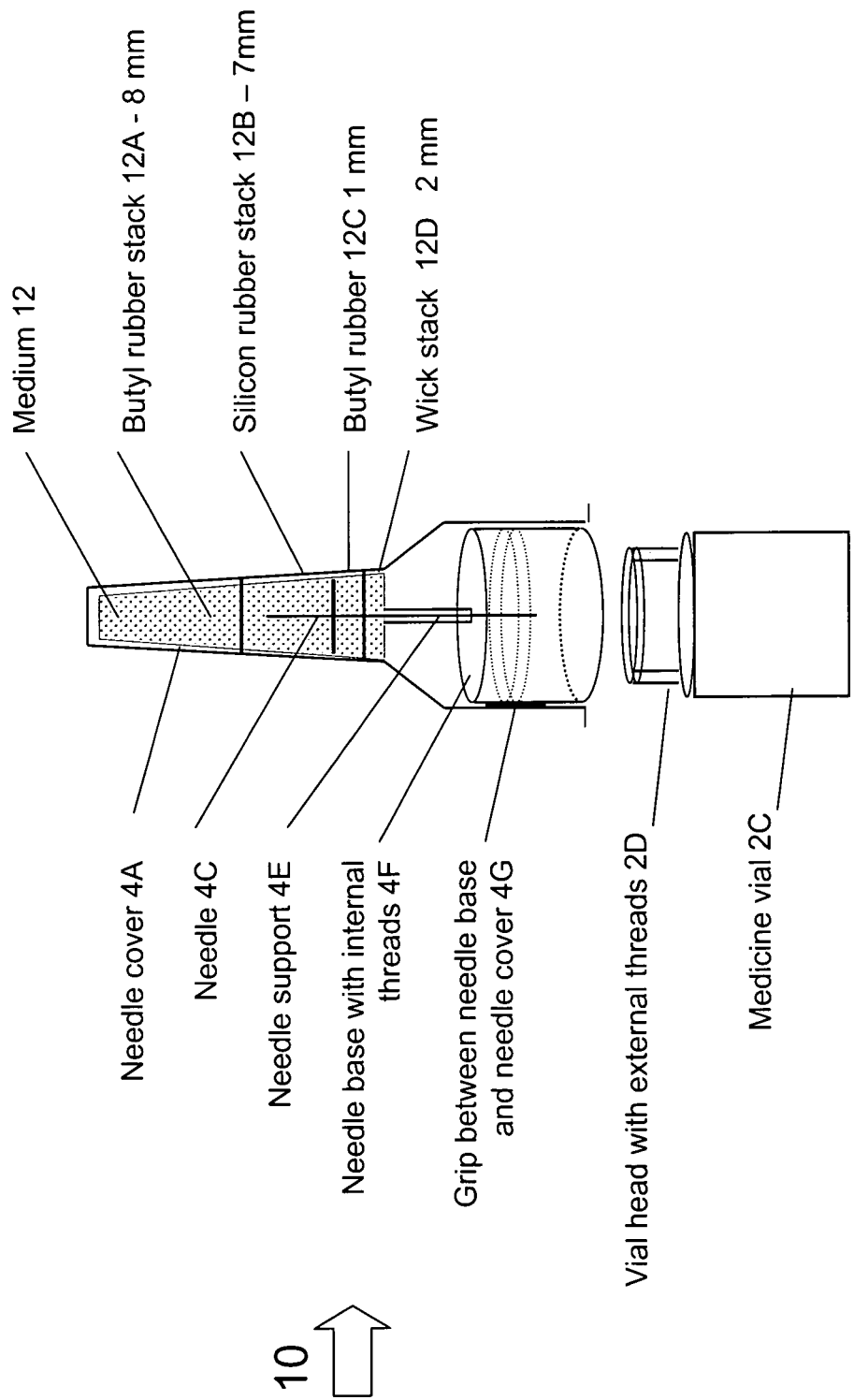
Figures 1, 2, 2C:
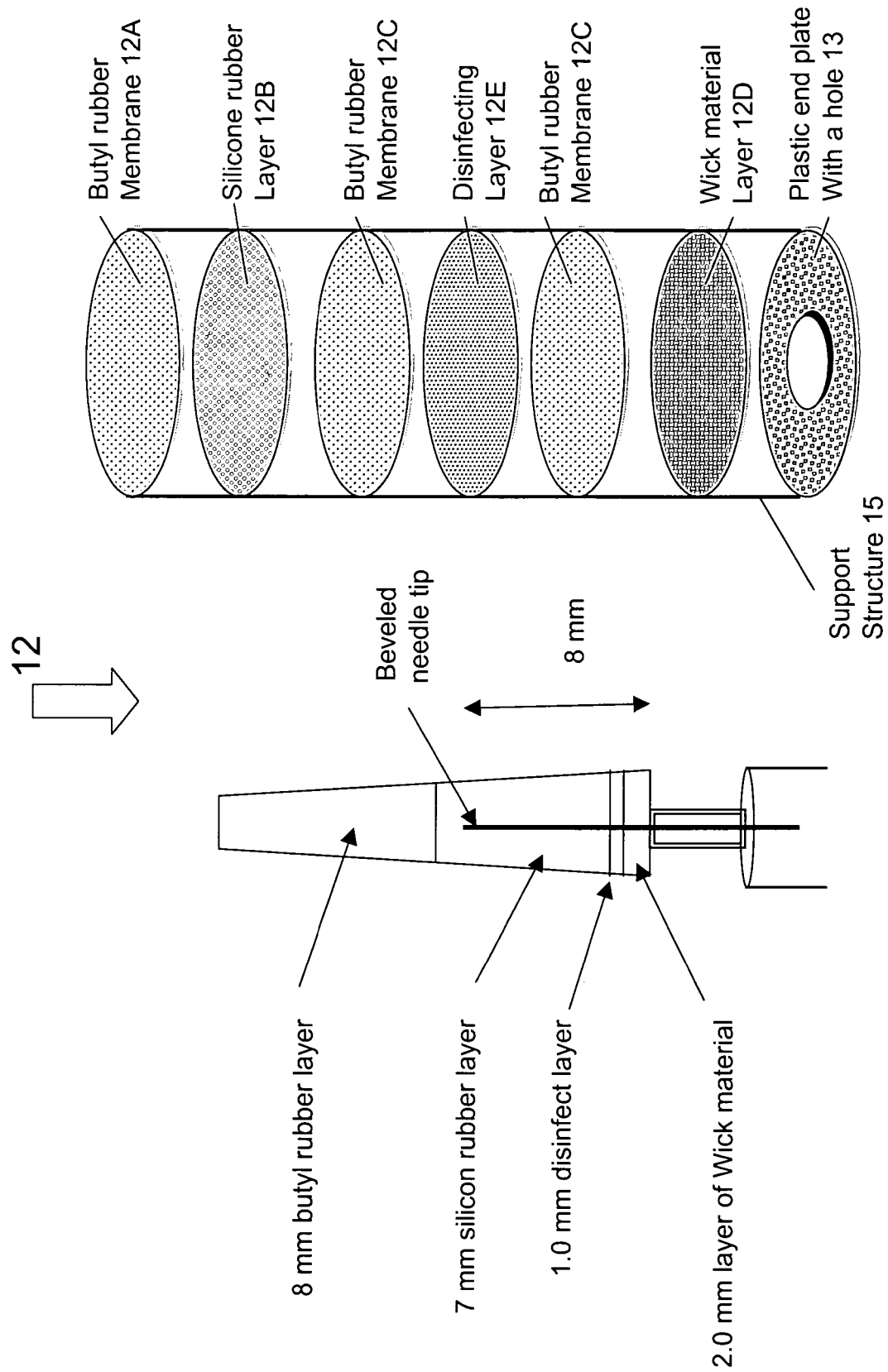
Figure 2D:
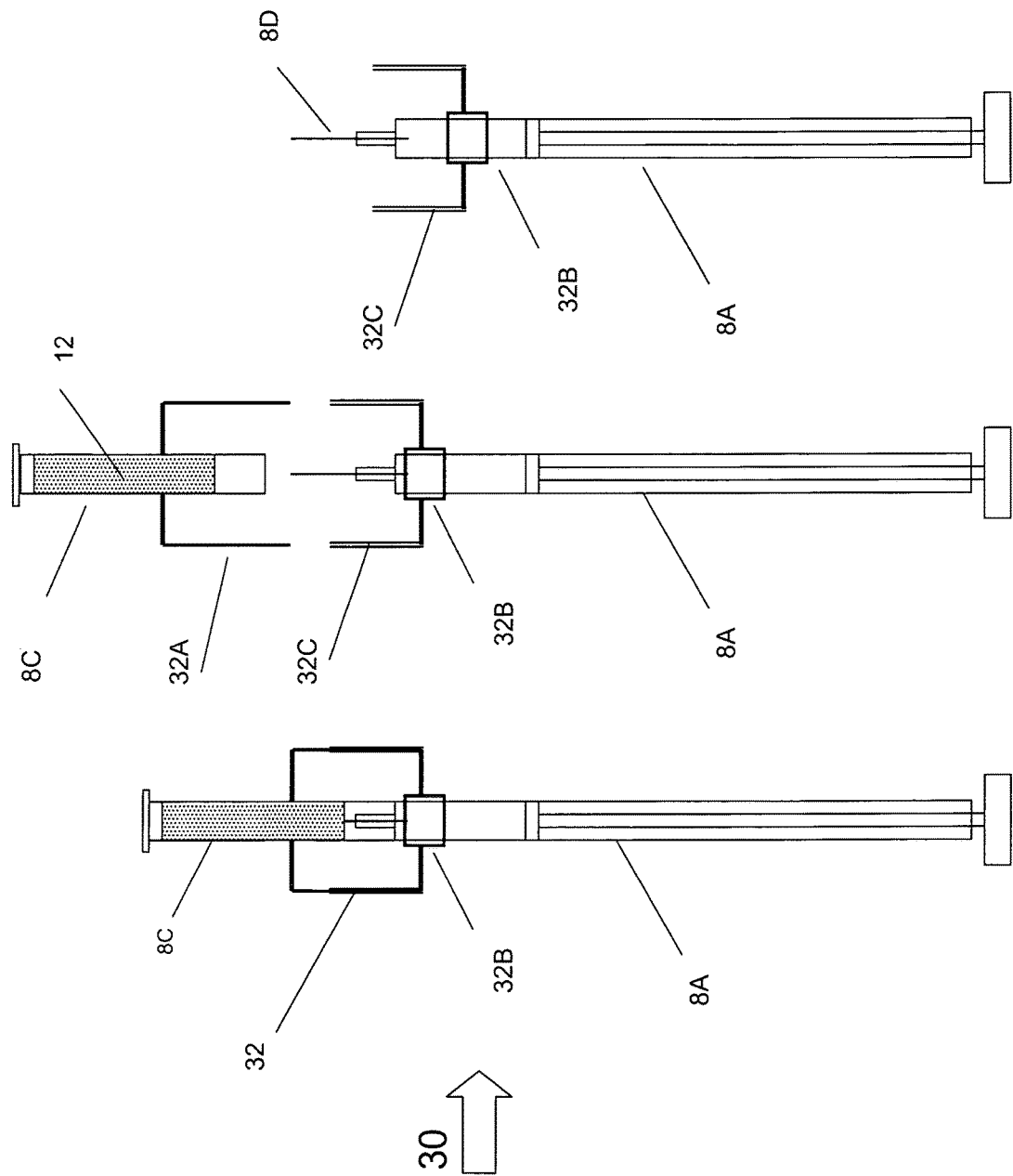

FIGS. 2A and 2B illustrate features of embodiment 10 for needles 4 used with pen injectors 2 as in prior art FIG. 1A. FIG. 2D illustrates embodiment 30 used with syringes 8 with attached needles as in prior art FIG. 2C.

Each of these embodiments 10 and 30 use a needle storage medium (NSM) 12 inside the needle cover. With reference to FIGS. 2C-1 and 2C-2, the needle storage medium (NSM) 12 is described first. After that how the NSM 12 is used inside the needle cover 4A of needle 4 and needle cover 8A of the syringe 8 is described.

The NSM 12 is a needle storage medium that is used inside a needle cover for preparing a needle for reuse. The NSM 12 is preferably made of a stack of mediums which are stacked on top of each other. The NSM 12 may have a support structure that help hold these stacks in place and facilitate insertion and positioning of the NSM inside a needle cover.

The NSM 12 is sized to the diameter and the height of the inner dimensions of a needle cover. The needle cover may be the same size as the prior art needle covers 4A and 8A or the needle cover may be made a certain size to accommodate a desired size of the NSM.

The diameter size of the NSM stack is a function of the space inside the needle cover and may be 3 to 5 mm. It may also be more or less than these sizes. The height of the NSM stack is approximately 15 to 20 mm. and is a function of the height of the needle and the height of the needle cover. The disposable industry manufacturers needle in various lengths such as, a 5 mm, an 8 mm, and a 12 mm for home users. However, an 8 mm needle length is the more common size for most home users.

FIG. 2C-1 illustrates the use of a NSM stack inside a needle cover on a needle. FIG. 2C-2 illustrates the details of the NSM stack itself. What is shown in FIG. 2C-1 is an 8 mm needle inside a NSM stack with the NSM stack inside the needle cover. What is also shown are four items of NSM stack with their probable thicknesses. The first stack is a wick stack of 2 mm thick, a disinfect stack of 1 mm thick and a lubricate stack of 7 mm thick and a rubber cap of 8 mm thick.

FIG. 2C-2 shows details of the construction of the NSM 12. With reference to FIG. 2C-2, the first item in the NSM stack from the bottom of the stack is a plastic disc 13 with an opening in the middle. The disc 13 is attached to and is part of a support structure 15. The support structure 15 may have vertical thin wire or strip like semi-rigid members to hold the stack layers of the NSM 12. Alternatively the support structure may be a cup or a cone or a cylinder that can hold and confine these different materials or mediums of stacks The second item of the stack is a wick medium 12D. The third item of the stack is a butyl rubber membrane 12C. The fourth item of the stack is a disinfecting medium 12E. The fifth item of the stack is a butyl rubber membrane 12C. The sixth item of the stack is a silicon rubber medium 12B. The seventh and last item of stack is a butyl rubber layer 12A.

The principle layers of the NSM stack are the wick layer 12D, a disinfect layer 12E and a lubricating layer 12B. The butyl rubber layers 12C provide a means to separate these three functioning layers. Butyl rubber is a synthetic rubber or an elastomer. Butyl rubber is impermeable to air and used in many applications requiring an airtight rubber.

Butyl rubber is a copolymer of isobutylene with isoprene. Polyisobutylene, also known as "PIB" or polyisobutene, $(C_4H_8)_n$, is the homopolymer of isobutylene, or 2-methyl-1-propene, on which butyl rubber is based. Butyl rubber is produced by polymerization of about 98% of isobutylene with about 2% of isoprene. The butyl rubber is the most widely used rubber in medical fields for rubber stoppers and as a cap on the liquid medicine bottles.

The wick layer 12D is used to wick up any remnant of the liquid from the tip of the needle as the needle is pushed through this NSM stack. The disinfectant layer 12E disinfects the needle, as the needle is pushed up through this stack. The lubricating layer 12B is used to provide a lubricating medium to lubricate the needle.

The disinfectant and lubricating medium may be combined as one medium where both of these functions may be provided by silicone rubber made for this application. The top stack of butyl rubber 12A along with the first stack of plastic disc 13 is intended to provide structure support to the other three functioning layers.

Many types of wicking material are used in the industry for many applications. An illustrative example of such a wick material is that used on a test strip of a glucose meter. When a drop of blood is touched the end of the strip, the blood drop is immediately wicked up the sensor area of the test strip.

Wicking works based on the capillary action. A wick is made of fibrous material that provides tiny tube like structures in the fiber. In the wick stack 12D, multiple layers or folds of wick material may be used. The wick layer 12D may be as much as ½ to 2 mm thick to provide a suitable quantity and type of wick to be able to function for the task of removing excess or remnants of the liquid on the tip of the needle left there from a last use of the needle in the body.

The disinfect stack 12E layer may be ½ mm to 2 mm thick and may have a medium in the form of a gel or other suitable density medium that stays confined in the stack and when the needle is pushed through it, the stack disinfects the needle. The stack may be a dense cotton material suffused with a suitable disinfecting agent for this purpose. It may also be rubber like medium with disinfecting properties.

The use of these disposable needles is confined to a home user. They are not meant for or used between different users. Therefore, the risk of infection from one user to the next user or between users is not present. These needles are used in soft fat tissue and not inserted in the blood stream. That also minimizes the risk of infection. Yet further an alcohol swab is used at the place of injection to disinfect the body area. Further, the needle injection is used at a protected or unexposed area of the body such as stomach or a thigh or a hip and is covered by clothing and thus not easy amenable to infection. Hence, the risk of infection form reuse of needles for the reasons as above is negligible. That risk is further negligible or non-existent, specifically after the needle has been sanitized and disinfected by the NSM.

The lubricating stack 12B may be made of a silicone based lubricant or a silicone rubber compound. Silicone is widely used material in many industrial applications including the medical, pharmaceutical and cosmetic industry. The lubricant that is applied to the needles in the process of manufacture is bonded to the steel of the needle and not likely to be worn out with insertion in soft fat tissue of the body. Never the less this stack provides for a means to lubricate the needle including the tip of the needle.

Silicones are inert, synthetic compounds with a wide variety of forms and uses. Typically heat-resistant and rubber-like, they are commonly used in medical applications, sealants, adhesives, lubricants, insulation, and breast implants.

Silicones are polymers that include silicon together with carbon, hydrogen, oxygen, and sometimes other chemical elements. Some common forms include silicone oil, silicone grease, silicone rubber, and silicone resin.

Dow Corning provides a medical grade dispersion product MDX4-4159, a 50% medical Grade dispersion. The Product description is that it is 50% active functional silicone polymer diluted in aliphatic isopropanol solvents. The features and uses are:

Room temperature curable coating

Chemical functionality that attracts the coating to metal and some plastic surfaces More substantive coating on metal surfaces than pure polydimethylsiloxane (PDMS) fluid Acceptable for lubricating hypodermic needles.

Dow Corning® MDX4-4159 Fluid, 50% Medical Grade Dispersion is used as a lubricant for cutting edges, including razor blades, scissors and hypodermic needles.

Dow Corning also manufacturers medical grade silicone fluids Dow Corning® 360 Medical Fluid 20, 100, 350, 1000, 12500 cSt with product description of Clear, colorless polydimethylsiloxane (PDMS) fluid and uses of Siliconization lubricant and Hydrophobic lubricant for glass, metal, plastic and rubber Dow Corning® also makes Medical Grade Fluid Emulsion 365, 35% Dimethicone NF Emulsion with Excellent lubricating and release characteristics as well good wetting characteristics.

For these reasons, it is believed that silicones and/or a silicone rubber form a desirable medium for the lubricating stack 12B.

As illustrated in FIG. 2A, a needle cap 14 may be used to store the needle with NSM after reuse. Such a cap 14 is in lieu of needle sealer 4D and protects the end of the needle used for insertion in the stopper of the medicine vial head 2B.

For the syringe injectors 8A, as illustrated with the help of FIG. 2D, to make the use of needle cover 8C with NSM 12 inside it, easier as it requires the needle cover 8C to be used on the needle 8D repeatedly, a needle cover guide 32 is described here. The guide 32 has a male guide part 32A attached to the needle cover 8C and a female guide part 32C attached to the syringe body 8A.

The needle cover 8C, attached to the male guide part 32A slides into the female guide part 32C which is attached to the syringe body 8A with the help of a collar guide 32B. The collar guide 32B enables the guide part 32C to be moved up and down the syringe body 8A, if required. When the needle cover 8C with the NSM 12 inside, with the attached guide part 32A is brought on top of the guide part 32C, the needle cover 8C is automatically centrally aligned to the tip of the needle 8D. Thus the guide 32 makes it easier to put the needle cover 8C with the NSM to be used to cover the needle 8D for next reuse.

The number of reuses of a needle with the NSM is limited to the quantity of the medicine supply available in a pen device or the medicine in the bottle for syringes. The quantity in a pen vial is 300 units. As much as 10 to 20 units may be injected 2 to 3 times in a day, providing approx 15 to 30 day worth of supply in a single pen. Similar quantity is in a bottle for use with the syringes. Hence for an average user, the needle reuse number in a month is approximately 90 reuses. The reuse of NSM is limited to reuses of up to 100 maximum.

There is no requirement to reuse a same NSM for an entire vial of medicine. Hence the reuse may be limited to any number less than 100, such as 10, or 20, 25 or 35 or 50 etc. To how many reuses of a needle an NSM stack may be limited, is believed to be a function of the design and properties of the NSM.

A supply of replacement needle covers 4A or 8A with the NSM 12 inside it may be sold in the aftermarket. If a needle cover with an NSM is used ten times that would lead to a reduction in the use of disposable needles and the corresponding cost of disposing sharp medical waste a ten fold. If the NSM is reused 25 times, a corresponding 25 fold reduction in the cost of disposable needles and sharp medical waste is expected.

What may be sold in the aftermarket for the syringe type injectors would be a needle cover with a NSM inside it and a guide for the needle cover. These would be used with the existing syringes in the market that are sold by manufacturers of these syringes.

What may be sold in the aftermarket for the pen-device injectors would be a needle cover with NSM inside along with a replacement pen device housing cover. This pen cover holds the needle when the needle is not in use as well as function as a guide for the needle cover when using with a needle. This pen cover would be used in place with the pen cover that came with the pen-device. When the NSM is used up based on number of uses as provided in the instructions for the use of the needle cover and the NSM, the old needle cover with the NSM would be discarded and replaced by a new needle and a new needle cover with the NSM.

Alternatively, instead of refreshing both the needle and the needle cover with the NSM, only a needle cover with NSM may be refreshed. While use of a NSM may be limited to a fewer number then the number of reuses of a needle, this may allow the number of reuses of the needle to be increased, providing a further benefit in the reduction of the sharp medical waste.

For the pen type injectors, the embodiment 20 illustrated with the help of FIGS. 3A, 3B, 4 and 5 provides for a guide mechanism for the needle cover 4A to be guided onto the needle 4D as well as a mechanism to store the needle on the pen injector itself.

Figure 3A:
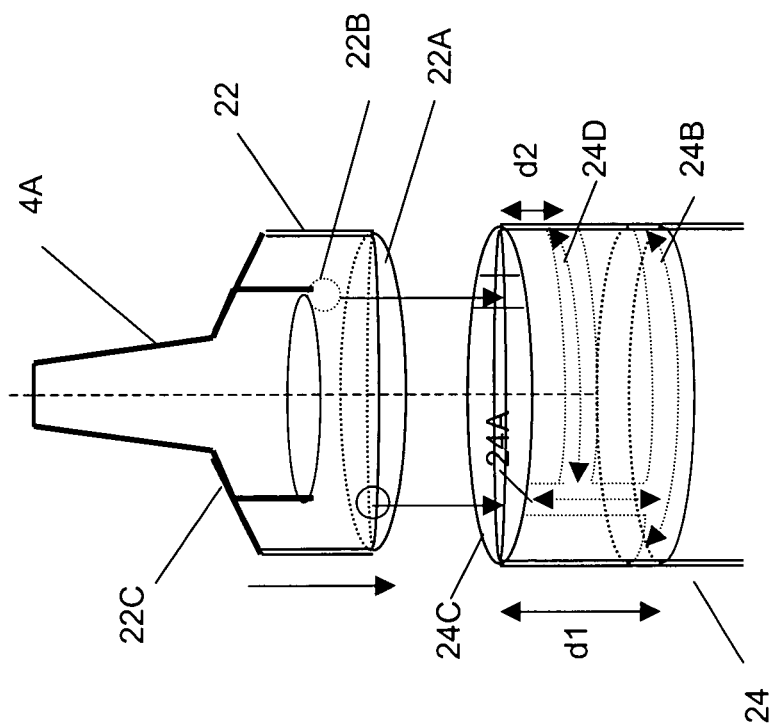
FIG. 3A-3B are block diagrams that illustrates features of a preferred embodiment for use of a needle with a pen delivery system.
Figure 3A:
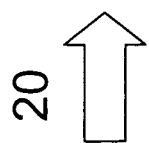
Figure 3B:
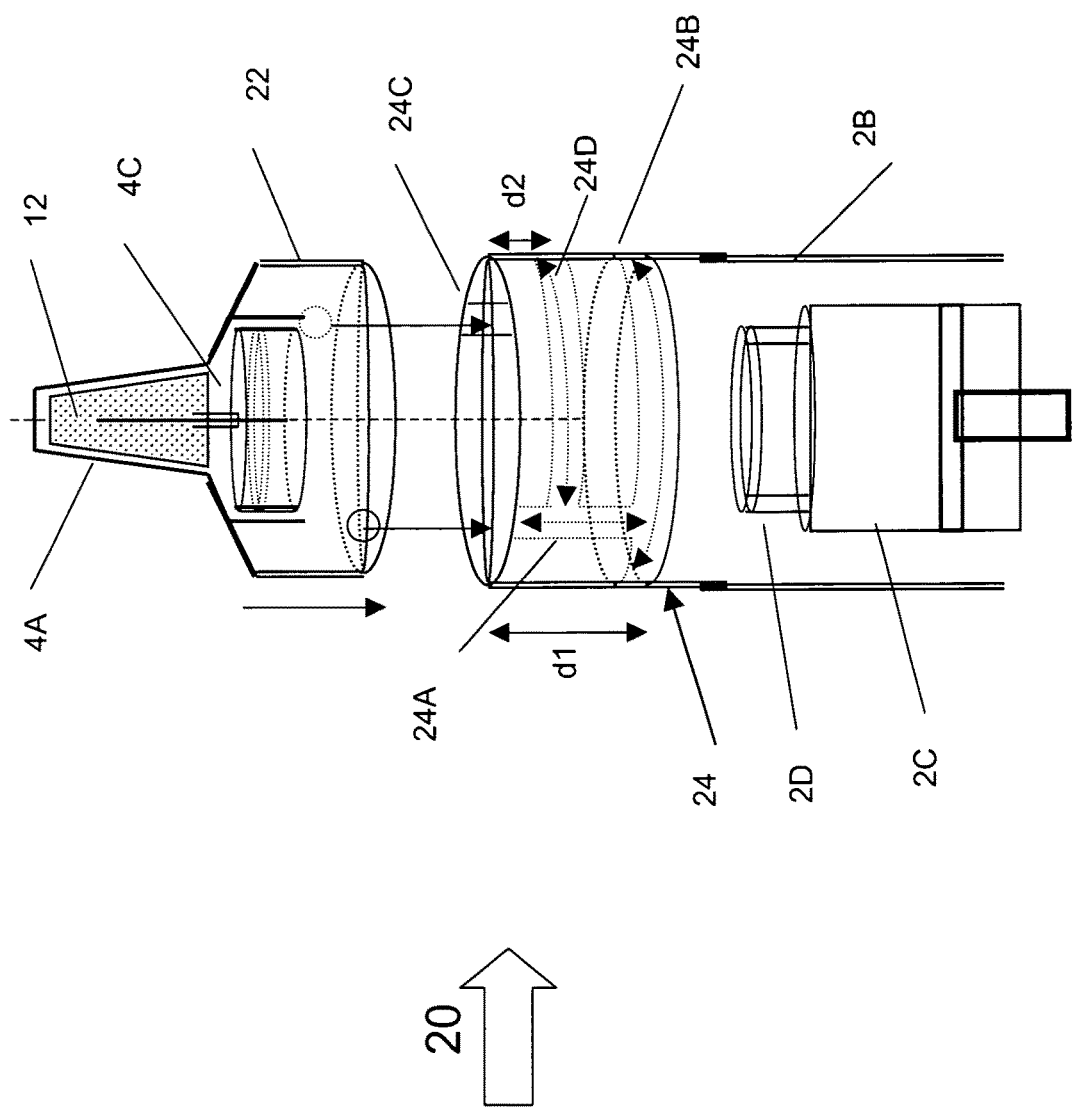

With reference to FIGS. 3A and 3B a needle cover 4A for the pen injectors is illustrated. FIG. 3A illustrates the needle cover 4A without the needle and the NSM inside. FIG. 3A also shows the open cover 24 of the pen without the vial inside it. FIG. 3B illustrates the needle cover 4A with the needle 4C and the NSM 12 inside the needle cover. The open pen cover 24 is shown with the pen cover 2B, the vial 2C with the vial head 2D.

As illustrated in FIGS. 3A and 3B, the needle cover 4A is provided an apron 22. The apron 22 has the features of an outsize circumference diameter 22A, a set of guide button 22B spaced around the circumference 22A. The apron 22 is fixedly attached 22C to the needle cover 4A as shown. The open end circular part 24 of the pen cover 2B has a circumference diameter 24C.

The circumference 24C is more than the circumference 22A so that the apron 22 of the needle-cover 4A would be guided into the part 24 with the help of the guide buttons 22B situated on the outside of the apron 22 and corresponding vertical grooves 24A situated on the inside of the part 24 and beginning from the tip of the circumference 24C.

The part 24, in addition to the vertical oriented groves 24A, also has a circular groove 24B at a depth of d1 from circumference tip 24C and another partial circular groove 24D at a depth of d2 from the circumference tip 24C.

The operation and function of the guide buttons 22B on the apron 22 and the vertical grooves 24A and circular grooves 24B on the part 24 are for guiding the needle cover 4A inside the pen-device cover 2B to the vial head 2D for the purpose of screwing the needle 4C to the vial head 2D and for storage of the needle 4C when not in use in the same cover 24. These features are further illustrated with the opened out drawings as in FIGS. 4 and 5A-J.

Figure 4:
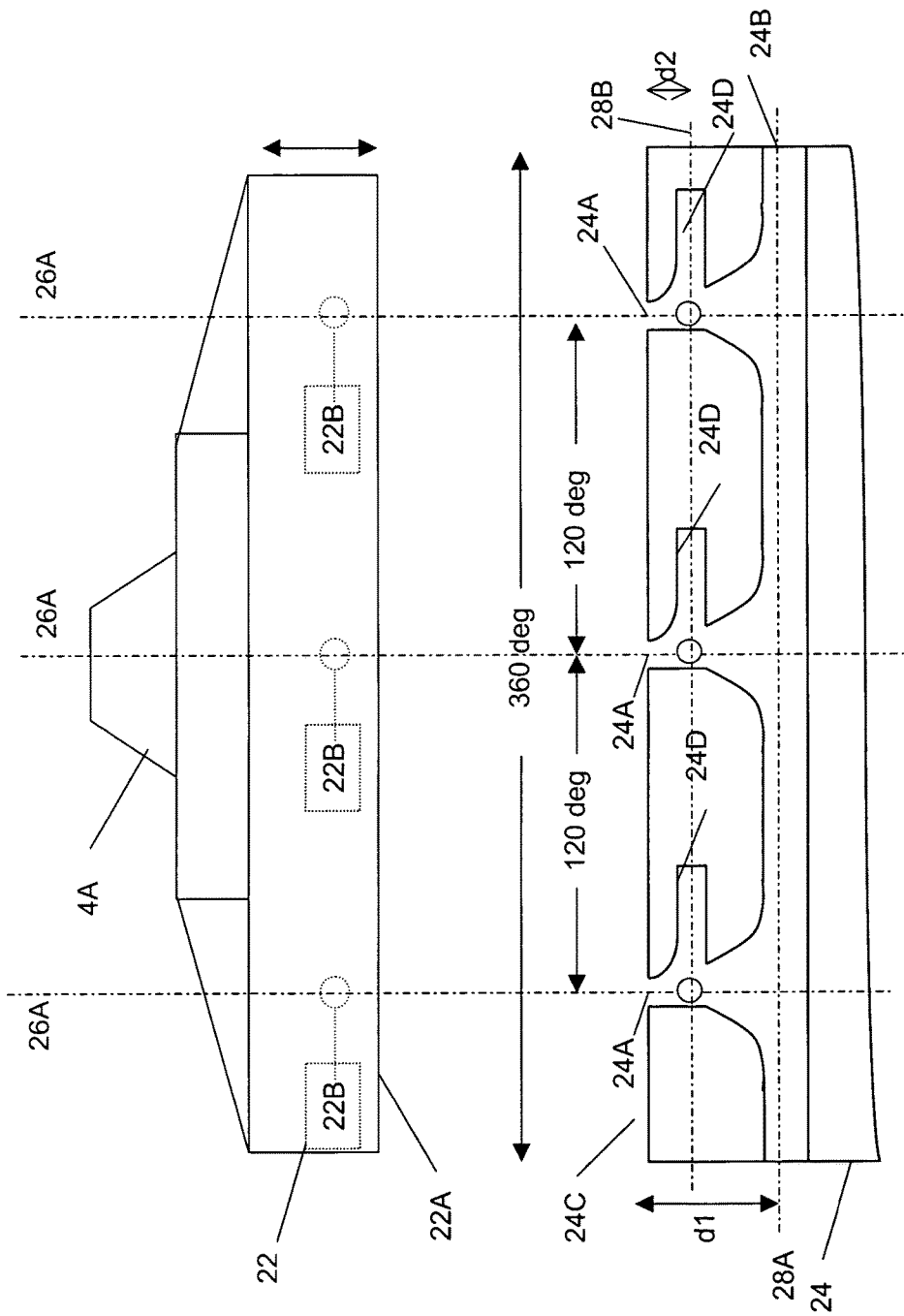
FIG. 4 is opened out block diagram that illustrates features of a preferred embodiment for use of a needle with a pen delivery system.

As illustrated in FIG. 4, an opened out view of the circular needle cover 4A with the apron 22 and circular pen cover 24 are illustrated. In the cover 4A, the apron 22, the opened out circumference 22A and three guide buttons 22B are shown. Also shown are the vertical guide axis 26A for the three guide buttons 22B that align the buttons 22B with the three corresponding vertical grooves 24A in the cover 24. The cover 24 is shown with the opened out circumference 24C and the three vertical grooves 24A spaced 120 degree apart on the circumference 24C.

Also shown are the partial horizontal circular grooves 24D along the axis 28B at a depth of d2 from the circumference tip 24C. Also shown is the circular groove 24B along the axis 28A at the depth of d1 from the circumference end 24C.

The operational features of these guide buttons 22B in apron 22 and guide groves 24A, 24B and 24D in the pen-device cover 24 are illustrated with the help of FIGS. 5A-K.

Operational Features of Guide Mechanism 22 and 24:

FIG. 5A shows the buttons 22B that are in position in the storage groove, when the needle is not in use and is stored in the pen cover 24.

FIG. 5B shows the position of the guide buttons 22B when the needle cover 4A is twisted clockwise for removing it from the storage position and then pushed down as shown in FIG. 5C to be in the circular groove at depth d1. In FIG. 5C, the needle 4C inside the needle cover 4A is sitting on top of the vial head 2D.

FIG. 5D shows when the needle cover is twisted clockwise to screw on the needle 4C to the vial head 2B as each has threads. As the needle 4C is being screwed on to the vial head 2D, it requires three turns and thus moves down in the circular groove 24B. The move down of the needle 4C on the vial head 2B for the three turns is around 2 mm. The depth of the circular groove 24B is sized to accommodate this travel down from the depth d2 to d2 plus 2 mm. delta.

When the screwing down of the needle onto the vial head is completed the guide buttons on the apron 22 align themselves with the bottom of the grooves as shown in FIG. 5E. The bottom of the vertical grooves 24A are flared to guide and enable the needle cover 4A to be pulled up the grooves 24A to separate the needle cover 4A from the needle 4C.

As shown in FIG. 5F, the needle cover 4A is almost at the top ready to be completely separated from the pen 2 cover 2B part 24, leaving only the needle 4C inside attached to the vial head 2D, ready for the needle to be used for an injection. As shown in FIG. 5G, the needle cover 4A is separated from the pen cover 24.

When the injection is completed, the needle cover 4A with the guide buttons 22B is guided back in the grooves 24A as shown in FIG. 5H. As shown in FIG. 5I, the needle cover is pushed all the way down to engage the needle 4C and then the needle cover is twisted counter clockwise three turns to unscrew the needle 4C from vial head 2D as shown in FIG. 5J.

Figure 5K:
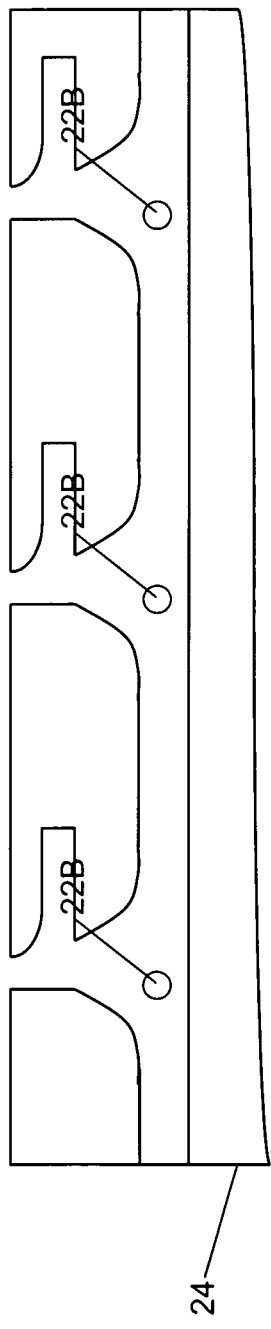
Figure 5L:
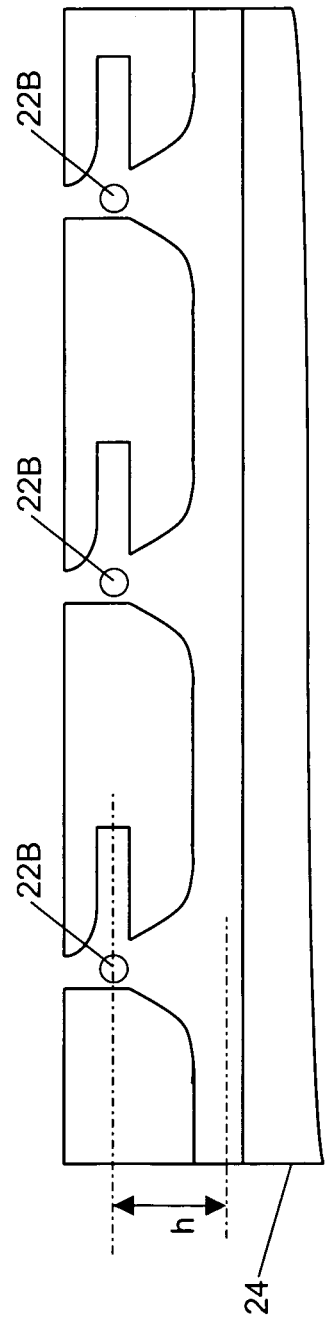

As the needle cover 4A is unscrewed from the vial head, it moves up by around 2 mm. The distance from the circumference tip 24C to the circular groove 24B allows for this vertical motion. As shown in FIG. 5K, after the unscrewing is completed, the buttons 22 align with the flared bottom of the vertical grooves 24B. Then the needle cover 4A, now with the needle 4C inside is pulled up the vertical grooves to a height h as shown in FIG. 5L.

Figure 5M:
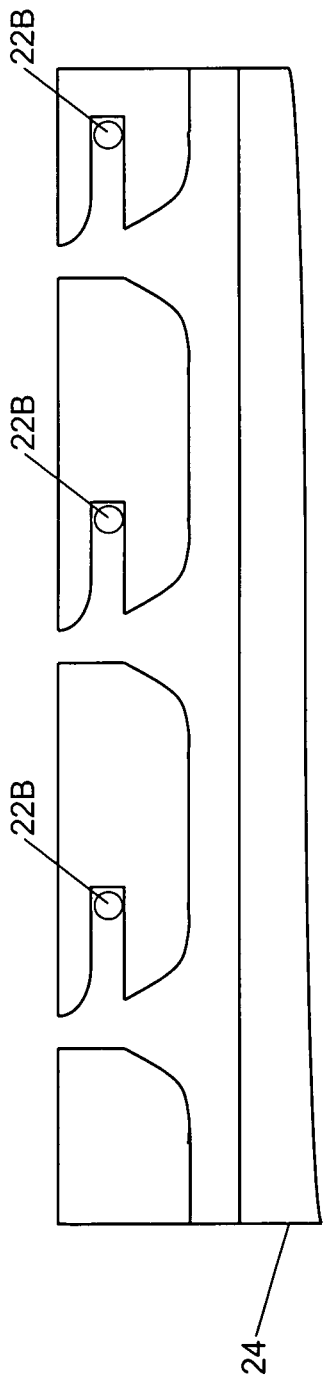

Then the needle cover 4A with the needle 4C inside is then twisted counter clockwise to lock and store in the storage position in grove 24D as shown in FIG. 5M.

Thus, as illustrated above, the needle cover 4A with the attached apron 22 is guided into and out of the open pen cover part 24 to mount and dismount the needle 4C onto and from the vial head 2B. Further with the help of the storage groove 24D, the needle cover with the needle inside is stored on the pen open cover 24 for reuse later on. Thus this one compact device, functions to guide the needle 4C to the vial head 2B, screw on the needle, remove the needle and then store the needle on the pen itself.

These above are simplified illustrations of a guide mechanism for guiding the installation and removal of needle on the vial head for the pen type injectors. There may be other or different type of such guide mechanism and these are not ruled out.

Figure 6A:
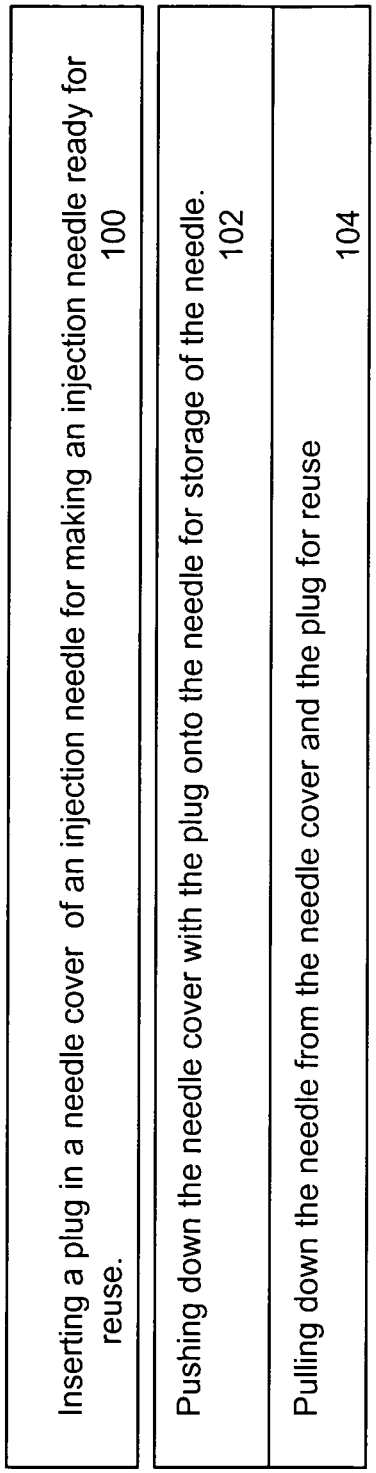

The method steps are as follows and illustrated with the help of FIGS. 6A, 6B and 6C, where all the steps may not be used or used in the order listed here. As shown in FIG. 6A:

At step 100, inserting a NSM in a needle cover of an injection needle for making an injection needle ready for reuse.

At step 102, pushing down the needle cover, with the NSM inside, onto the needle for storage of the needle.

At step 104, pulling down the needle from the needle cover and the NSM plug for reuse.

With reference to FIG. 6B, the steps are:

At step 106, having a needle cover for an injection needle;

At step 108, positioning a NSM inside the needle cover;

At step 110, inserting the needle cover and the NSM on the needle.

At step 112, removing the injection needle for next use.

At step 114, having in the NSM wicking, disinfecting, and a lubricating mediums.

At step 116, having a guide mechanism for guiding the needle inside the needle cover.

At step 118, having a sliding guide mechanism for guiding the injection needle inside the needle cover for injection needles mounted on syringes.

At step 120, having a (i) sliding guide mechanism for guiding the removal and installation of the needle cover with the injection needle inside, to a vial head of a pen dispenser and (ii) a rotary mechanism for screwing and unscrewing the needle inside the needle cover on to and from the vial head, for injection needles made for a pen dispenser use.

At step 122, having a storage mechanism for the needle cover with the needle inside in a housing of the pen dispenser.

As illustrated in FIG. 6C, a method of manufacturing a device for reuse of injection needles, comprising the steps of:

At step 124, molding an injection needle cover with a guide mechanism in the needle cover for guiding the needle cover on to a needle;

At step 126, inserting a needle storage medium inside the needle cover.

At step 128, molding a male part of the guide mechanism in the needle cover and a female part in the syringe for a syringe injector.

At step 130, molding a male part of the guide mechanism in the needle cover and a female part in the pen injector housing.

An apparatus for injection needle has a device that enables reuse of a single-use injection needle for multiple injection uses for a same user. The device has a needle cover with a disinfecting agent, a sanitizing agent and a lubricating agent that are positioned inside the needle cover. The needle cover sanitizes, disinfects and lubricates a single-use injection needle for reuse when the needle is moved inside the needle cover and positioned therein for temporary storage.

The agents are held in a medium that enable the agents to be positioned inside the needle cover. The agents in the medium are stacked on top of each other in heights for different needle lengths. The first stack is a wick medium that absorbs excess fluid droplets from a needle head, the second stack is a medium that disinfects the needle, and the third stack is a medium that lubricates the needle.

The height of stack is greater than the height of the needle. The wick height is ½ to 2 mm, the disinfectant height is ½ to 2 mm and the lubricate height is 4 mm to 12 mm. The wick is made of wick material, the disinfectant is made of butyl rubber, and the lubricate medium is made of silicone rubber.

The device has a guide for storage of the needle cover when the needle is not in use. The guide engages the needle cover with a syringe housing to store the needle cover for later reuse on the syringe itself.

In another embodiment, an apparatus for injection needle has a device that enables reuse of a single use injection needle for multiple injection uses for a same user. The device a needle cover, a disinfecting agent, a sanitizing agent and a lubricating agent that are positioned inside the needle cover, where the needle cover sanitizes, disinfects and lubricates the needle for reuse when the needle is moved inside the needle cover and positioned therein. A cylindrical housing of a medicine vial has grooves that position and slide the needle cover in the housing for preparing the needle for reuse and storage.

The vial housing has anterior grooves that position and slide the needle cover in the housing of the vial for (i) mounting the needle on to a vial head for use, (ii) separate the needle cover from the housing to expose the needle for injection use, (iii) dismounting the needle from the vial head after use, and (iv) for storing the needle inside the needle cover for subsequent reuse.

The grooves on interior surface of the vial housing enable a vertical slide motion and a circular rotation motion of the needle cover inside the housing. The vertical slide enable the needle cover with the needle inside the cover to be moved into and away from the vial head and the circular motion enable the needle to be threaded on to the vial head and unthreaded from the vial head. A storage groove enables the needle cover with the needle to be stored attached to the housing.

The grooves are positioned on interior surface of the vial housing and corresponding part is positioned on the outside of the needle cover enabling the needle cover to be inserted inside the housing for sliding in a vertical direction and be rotated in both a clockwise and a anti-clockwise direction.

In summary, the preferred embodiments are for an apparatus for injection needle that has a device that enables reuse of a single-use injection needle for multiple injection uses for a same user. The device has a needle cover with a disinfecting agent, a sanitizing agent and a lubricating agent that are positioned inside the needle cover. The needle cover sanitizes, disinfects and lubricates a single-use injection needle for reuse when the needle is moved inside the needle cover and positioned therein for temporary storage. The agents are held in a medium that enable the agents to be positioned inside the needle cover. The agents in the medium are stacked on top of each other in heights for different needle lengths. The first stack is a wick medium that absorbs excess fluid droplets from a needle head, the second stack is a medium that disinfects the needle, and the third stack is a medium that lubricates the needle.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for facilitating reuse of a single-use injection needle for multiple injection uses for a same user, the apparatus comprising:
   a needle cover with a first stack as a wicking medium to absorb excess fluid droplets, a second stack as a disinfecting agent to disinfect the single-use injection needle, and a third stack as a lubricating agent to lubricate the single-use injection needle that are positioned inside the needle cover, wherein the wicking medium, the disinfecting agent, and the lubricating agent are stacked on top of each other in heights for different needle lengths;
   a guide mechanism that guides the needle cover onto the single-use injection needle;
   wherein the needle cover sanitizes, disinfects and lubricates the single-use injection needle for reuse when the single-use injection needle is moved inside the needle cover and positioned therein for temporary storage.

2. The apparatus, as in claim 1, comprising:
   the disinfecting agent is held in a medium that enables the disinfecting agent to be positioned inside the needle cover.

3. The apparatus, as in claim 1, comprising:
   the wicking medium absorbs the excess fluid droplets from a needle head to clean the single-use injection needle.

4. The apparatus, as in claim 1, comprising:
   the guide mechanism is configured for storage of the needle cover with the single-use injection needle inside when the single-use injection needle is not in use.

5. The apparatus, as in claim 4, comprising:
   the guide mechanism is attached to a syringe body of a syringe to store the needle cover in the guide mechanism for later reuse on the syringe.

6. An injection needle apparatus, comprising:
   a pen needle for injection, wherein the pen needle has a needle cover, wherein the needle cover when positioned over the pen needle, cleans, disinfects and lubricates the pen needle for reuse for a same user;
   the needle cover has positioned inside, a first stack as a wicking medium to absorb excess fluid droplets, a second stack as a disinfecting agent, and a third stack as a lubricating agent, wherein the wicking medium, the disinfecting agent, and the lubricating agent are stacked on top of each other in heights for different needle lengths;
   a guide mechanism uses a cylindrical housing of a medicine vial that has grooves that position and slide the needle cover in the cylindrical housing for preparing the pen needle for reuse and storage; and
   the pen needle, when moved inside the needle cover, first moves through the first stack, then the second stack, and then the third stack, thereby the needle cover cleans, disinfects and lubricates the pen needle for reuse by the same user.

7. The injection needle apparatus, as in claim 6, comprising:
  wherein the grooves of the cylindrical housing of the medicine vial are anterior grooves that collectively position and slide the needle cover in the cylindrical housing of the medicine vial for (i) mounting the pen needle on to a medicine vial head for use, (ii) separating the needle cover from the cylindrical housing to expose the pen needle for injection use, (iii) dismounting the pen needle from the medicine vial head after use, and (iv) storing the pen needle inside the needle cover for subsequent reuse.

8. The injection needle apparatus, as in claim 7, comprising:
  a. wherein a first groove of the anterior grooves is on an interior surface of the cylindrical housing of the medicine vial and enables a vertical slide motion and a second groove of the anterior grooves is on the interior surface of the cylindrical housing of the medicine vial and enables a circular rotation motion of the needle cover inside the cylindrical housing;
  b. the vertical slide motion enables the needle cover with the pen needle inside the needle cover to be moved into and away from the medicine vial head and the circular rotation motion enables the pen needle to be threaded on to the medicine vial head and unthreaded from the medicine vial head;
  c. wherein a third groove of the anterior grooves is a storage groove, the storage groove enables the needle cover with the pen needle to be stored attached to the cylindrical housing.

9. The injection needle apparatus, as in claim 8, comprising:
  the anterior grooves positioned on the interior surface of the cylindrical housing and a corresponding part positioned on an outside of the needle cover enable the needle cover to be inserted inside the cylindrical housing for sliding in a vertical direction and rotation in both a clockwise and an anti-clockwise direction.

10. A method of preparing a pen injection needle, wherein the pen injection needle is used with an insulin pen, with a medicine vial with a dispense end and a cover over the dispense end of the medicine vial, for reuse for a same user, comprising the steps of:
  providing for the pen injection needle a needle cover;
  positioning inside the needle cover a needle storage medium (NSM) and storing the pen injection needle for the reuse inside the needle cover
  providing in the NSM when the pen injection needle is moved into the needle cover, a first stack as a wicking medium to absorb excess fluid droplets for cleaning the pen injection needle, a second stack as a disinfecting agent for disinfecting the pen injection needle, and a third stack as a lubricating agent for lubricating the pen injection needle that are positioned inside the needle cover, wherein in the NSM, stacking on top of each other the wicking medium, the disinfecting agent, and the lubricating agent in heights for different needle lengths;
  moving the pen injection needle, in the NSM, through the first stack comprising the wicking medium, then the second stack comprising the disinfecting agent and then the third stack comprising the lubricating agent inside the needle cover for temporary storage until a next use of the pen injection needle, wherein the needle cover cleans, disinfects and lubricates the pen injection needle for reuse when the pen injection needle is moved inside the needle cover and positioned therein for temporary storage until the next use of the pen injection needle and guiding the needle cover onto the pen injection needle using a guide mechanism.

11. The method, as in claim 10, comprising the steps of:
  holding the disinfecting agent and the lubricating agent in a physical medium that enables the disinfecting agent and the lubricating agent to be positioned inside the needle cover.

12. The method, as in claim 10, comprising the steps of:
  guiding the pen injection needle inside the needle cover for temporary storage of the injection needle inside the NSM until a next reuse of the pen injection needle.

13. The method, as in claim 12, where the guide mechanism is a sliding guide mechanism for guiding the pen injection needle inside the needle cover for injection needles mounted on syringes.

14. The method, as in claim 13, further comprising the steps of:
  having (i) the sliding guide mechanism for guiding removal and installation of the needle cover with the pen injection needle inside, to a vial head of a pen dispenser and (ii) a rotary mechanism for screwing and unscrewing the pen injection needle inside the needle cover on to and from the vial head, for injection needles made for a pen dispenser use.

15. The method, as in claim 14, comprising the steps of:
  having a storage mechanism, in a housing of the pen dispenser, for the needle cover with the pen injection needle inside the needle cover.

16. An apparatus for a syringe with a permanently attached injection needle that enables reuse of the syringe for multiple injection uses for a same user, comprising:
  a needle cover;
  the injection needle is stored for a reuse inside the needle cover, wherein the needle cover with an open end on one end and a closed end on an opposite end and positioned therein inside the needle cover, from the open end to the closed end, a first stack comprising a wicking medium to absorb excess fluid droplets for cleaning the injection needle, then a second stack comprising a disinfecting medium that holds a disinfecting agent, and then a third stack comprising a lubricating medium being a lubricating agent, wherein the wicking medium, the disinfecting agent, and the lubricating agent are stacked on top of each other in heights for different needle lengths;
  the injection needle first moves through the first stack comprising the wicking medium, then the second stack comprising the disinfecting agent, and then the third stack comprising the lubricating agent when the injection needle is moved inside the needle cover for temporary storage until a next use of the injection needle;
  the needle cover cleans, disinfects and lubricates the injection needle for reuse when the injection needle is moved inside the needle cover from the open end.

17. The apparatus as in claim 16, comprising:
  a. the injection needle is moved inside the needle cover and positioned therein for temporary storage until the next use of the injection needle;
  b. the needle cover cleans, disinfects and lubricates the injection needle for reuse.

18. The apparatus as in claim 16, comprising:
  the disinfecting agent and the lubricating agent are held in a physical medium that enable the agents to be positioned inside the needle cover.

* * * * *